US 7,151,598 B2

(12) United States Patent
Poponin

(10) Patent No.: US 7,151,598 B2
(45) Date of Patent: Dec. 19, 2006

(54) METHOD AND APPARATUS FOR ENHANCED NANO-SPECTROSCOPIC SCANNING

(75) Inventor: Vladimir Poponin, 1890 Sutter St., #204, San Francisco, CA (US) 94115

(73) Assignee: Vladimir Poponin, San Francisco, CA (US)

( * ) Notice: Subject to any disclaimer, the term of this patent is extended or adjusted under 35 U.S.C. 154(b) by 206 days.

(21) Appl. No.: 10/959,238

(22) Filed: Oct. 5, 2004

(65) Prior Publication Data

US 2005/0084912 A1 Apr. 21, 2005

Related U.S. Application Data

(63) Continuation-in-part of application No. PCT/US04/10544, filed on Apr. 5, 2004.

(60) Provisional application No. 60/460,702, filed on Apr. 4, 2003.

(51) Int. Cl.
*G01J 3/44* (2006.01)
*G01N 21/65* (2006.01)

(52) U.S. Cl. ............. 356/301; 435/287.2; 435/288.7

(58) Field of Classification Search ............. 356/301
See application file for complete search history.

(56) References Cited

U.S. PATENT DOCUMENTS

| 5,479,024 | A | 12/1995 | Hillner et al. |
| 6,002,471 | A | 12/1999 | Quake |
| 6,441,359 | B1 | 8/2002 | Cozier et al. |
| 6,850,323 | B1 * | 2/2005 | Anderson .............. 356/301 |

OTHER PUBLICATIONS

Copy of International Search Report from PCT Application No. PCT/US04/10544.

* cited by examiner

*Primary Examiner*—F. L. Evans
(74) *Attorney, Agent, or Firm*—Perkins Coie LLP

(57) ABSTRACT

Apparatus and method for examining the identity of chemical groups in a sample are disclosed. The apparatus has a substrate having a plasmon resonant surface on which the sample is supported, a source of a beam of light, and a lens assembly having a tip region and a nanolens composed of one or more plasmon resonance particles (PRPs) on the tip region. The PRPs are arranged to produce near-field electromagnetic gap modes in a space between the nanolens and a confronting detection region on the substrate surface when the gap between the nanolens and substrate is 30 nm or less. A focusing mechanism in the apparatus operates to move the lens assembly toward and away from the substrate surface, with a gap of less than 30 nm, to produce electromagnetic gap modes that enhance the Raman spectroscopy signals produced by the sample in the detection region.

18 Claims, 11 Drawing Sheets

METHOD AND APPARATUS FOR ENHANCED NANO-SPECTROSCOPIC SCANNING

This application is a continuation-in-part of PCT application Ser. No. PCT/US2004/010544 filed Apr. 5, 2004, which claims priority to U.S. Patent Application Ser. No. 60/460,702 filed Apr. 4, 2003, both of which are incorporated in their entirety herein by reference.

FIELD OF THE INVENTION

The present invention relates to the field of nano-spectroscopic scanning, and in particular, to a method and apparatus capable of spectroscopic identification of single-molecule or single-chemical group structures carried on a substrate.

REFERENCES

The references below are cited as part of the background of the invention and/or as providing methodologies that may be applied to certain aspects of the present invention. These references are incorporated herein by reference.

G. R. Brewer, Electron-Beam Technology in Microelectronic Fabrication, Academic Press, NY, 1980).

David Ginger et al., "The evolution of Dip-Pen Nanolithography", Angew. Chem. Int. Ed. ,v. 43, p. 30–45, 2004).

S. Hayashi, "Spectroscopy of Gap Modes in Meta Particle-Surface Systems," Tpoics Appl Phys 81:71–95 (2001).

I-K. Kneipp et al. "Ultrasensitive Chemical Analyses by Raman Spectroscopy", Chem. Rev., 1999, vol. 99, p. 2957–2975, see p. 271).

J. Li et al. "DNA molecules and configurations in a solid-state nanopore microscope", Nature Materials, vol 2, p611–615 (2003).

V. Matyushin, A et al., "Tuning the setup of sputter-coated multilayers in nanocluster-based signal enhancing biochips for optimal performance in protein and DNA-assays" J. Nanoscience and Nanotechnology Volume 4, Number 1/2 (January/February 2004), pp. 98–105 (2004)

D. McCamant, "Femtosecond Broadband Stimulated Raman: A new Approach for High-Performance Vibrational Spectroscopy", Applied Spectroscopy, Vol. 57, p. 1317–1323, 2003.

S. C. Minne et. al., "Automated parallel high-speed atomic force microscopy", Applied Physics Letters, Vol. 72, p. 2340–2342, 1998.

S. C.Minne et al., "Bringing Scanning Probe Microscopy up to Speed", 173 p. Kluwer Academic Publishers, 1999.

C. M. Niemeyer, "Self-assembled nanostructures based on DNA: towards the development of nanobiotechnology", Current Opinion in Chemical Biology, v. 4, p. 609–618, 2000.

J. Prikulis et all., "Optical Spectroscopy of Single Trapped Metal Nanoparticles in Solution", Nano Letters, v. 4, p. 115–118 , 2004

J. P. Rabe. "Self-assembly of single macromolecules at surfaces". Current Opinion in Colloid and Interface," Science. Vol. 3, p. 27–31, 1998

F. Wolf et al., Review of Scientific Instruments, 1999, Vol. 70, p. 2751–2757, "Novel Scanning Near-Field Optical Microscope (SNOM)/scanning confocal optical microscope based on normal force distance regulation and bent etched fiber tips."

Y. Xia et all., Advanced Functional Materials, v. 13, p. 907–918, 2003 "Template-assisted Self-Assembly of Spherical Colloids into Complex and Controllable Structures"

H. Xu et al. Phys Rev E, v. 62, p. 4318, 2000.

J. Xu et al. "Microfabricated Quill-Type Surface Patterning Tools for the Creation of Biological Micro/Nano Arrays", Biomedical Microdevices, v. 6, p. 117–123 (2004)

F. Zenhausen, et al., "Scanning Interferometric Apertureless Microscopy: Optical Imaging at 10 Angstrom Resolution", Aug. 25, 1995, Science, Vol. 269.

BACKGROUND OF THE INVENTION

A variety of tools and methods exist for examining surface features and structure at the microscale and even nanoscale level. Scanning probe microscopy (SPM) allows for mapping surface topology at a microscale level by moving a detector tip carried at the free end of a cantilever beam over or across the surface of the material being mapped. This type of microscope may operate by direct physical contact with the surface (scanning atomic force microscopy or AFM) or, in a tunneling mode, by detection of a tunneling current when the tip is at selected distance from the surface (scanning tunneling microscopy or STM).

These types of devices have proven very useful for mapping surface topography, e.g., for detecting imperfections in integrated-circuit chips, but is not designed or can be operated to detect specific chemical compounds or chemical groups. This concept has been extended to parallel-high-speed AFM (e.g., Minne, 1998; 1999).

The scanning tip approach has also been adapted for optical detection of mapping of a surface. U.S. Pat. No. 6,441,359, for example, describes a near-field optical scanning system in which near-field optics is carried at the free end of a cantilever beam. The patent also discloses microfabrication methods for constructing an array of such optical elements for an optical scanning system. The tip to sample distance in the apparatus is controlled by an optical level deflection system that acts to maintain the top close to the sample surface. The system is able to achieve sub-wavelength resolution by scanning an aperture of sub-wavelength dimensions or by scanning the solid immersion lens very close to the sample. The device is not designed nor could it be used to detect individual chemical molecules or groups, die to the very low signal level that would be produced. Scanning near-filed optical microscopes (SNOM) have been proposed by others (e.g., Wolf).

One very sensitive probe for chemical analysis is surface-enhanced Raman spectroscopy or SERS (see, for example Kneipp). In addition SERS has been applied to a high-resolution scanning microscope for purposes of achieving high-resolution spectroscopic information from a sample surface, e.g., U.S. Pat. No. 6,002,471. The device includes a small conductive element (a plasmon resonance particle or PRP) at the free tip of a scanning cantilever beam, to enhance the light emitted in the vicinity of the probe. The sample substrate is formed of glass. The patent does not show or suggest methods for exploiting electromagnetic gap modes to enhance spectroscopic resolution that is likely for resolving single chemical structures, such as DNA bases, nor does the patent show of suggest a system capable of reading a plurality of samples, e.g., stretch DNA strands, in parallel.

SUMMARY OF THE INVENTION

In one aspect, the invention includes an apparatus for examining the identity of chemical groups in a sample attached to a surface. The apparatus has a plasmon resonant substrate, i.e., a substrate having a mirror surface on which the sample is supported, a source of a beam of light, preferably coherent light, and a lens assembly having a tip region and a nanolens composed of one or more plasmon resonance particles (PRPs). The PRPs are arranged on the tip region to produce, when the light beam is directed through the nanolens, near-field electromagnetic gap modes in a space between the nanolens and a confronting detection region on the substrate surface, in a gap between the nanolens and substrate that is 40 nm or less.

A focusing mechanism in the apparatus, such as a piezoelectric drive, is operable to move the lens assembly toward and away from the substrate surface, with a gap therebetween of less than 40 nm, to produce electromagnetic gap modes that enhance the Raman spectroscopy signals produced by the sample in the detection region. Light emitted by or scattered from the sample at the detection region is received at a detector, which converts the received light into a characteristic Raman spectrum, whereby the sample chemical group at the detection region can be identified. The apparatus may include a translation mechanism, such as a piezoelectric drive, for translating the lens assembly relative to the substrate, to position the lens assembly over different detection regions of the substrate.

The nanolens in the assembly preferably includes at least said three PRPs arranged symmetrically about a central axis normal to the plane of the substrate surface, with each PRP being less than 50–200 nm in its largest dimension, and the distance across any pair of PRPs being substantially less than the wavelength of the light beam. The PRPs may be spherical, or ellipsoidal and arranged with their major axes oriented to intersect the central axis. The light source in this embodiment may produce a beam of circularly polarized light, preferably coherent light, whose plane of polarization is normal to the central axis.

The lens assembly may include a cantilever beam having a tip region at its free end, with the focusing mechanism being operatively coupled to the beam. The mechanism is preferably operable to bring the nanolens to a selected distance between 0.1 and 5 nm of the substrate surface.

For use in sequencing a linear strand of nucleic acid, by successively examining the bases (chemical groups) of the nucleic acid strand, the substrate includes molecular anchors for holding the nucleic acid strand in a stretched linear condition, and the translation mechanism is operable to move the lens assembly along the length of the strand, for examining and identifying each base of the strand sequentially. For examining a plurality of substantially nucleic acid samples simultaneous, the apparatus provides a plurality of linearly aligned cantilever lens assemblies, each of whose position toward and away from the substrate surface can be individually controlled by a corresponding focusing mechanism associated with each lens assembly, and which are translated as a unit by a single translation mechanism.

In another aspect, the method includes a method for examining the identity of chemical groups in a sample. After attaching the sample to a substrate having a plasmon resonant mirror surface, a beam of light is directed onto the sample through a nanolens in a lens assembly of the type described above, to produce near-field electromagnetic gap modes in a space between the nanolens and a confronting detection region on the substrate surface, when the gap between the nanolens and substrate is 40 nm or less. The lens assembly is moved toward or away from the substrate surface, with a spacing between the nanolens and substrate surface of less than 40 nm, to produce electromagnetic gap modes that enhance the Raman spectroscopy signals produced by the sample in the detection region. The light emitted by or scattered from the sample at the detection region is received by a detector and converted to a Raman spectrum that is characteristic of the chemical group being interrogated, whereby the sample chemical group at the detection region can be identified.

The position of the lens assembly may be controlled to bring the nanolens to a selected gap distance between 0.1 and 5 nm of the substrate surface. The nanolens may be composed of at least three PRPs arranged symmetrically about a central axis that is normal to the plane of the substrate surface, each particle is less than 50–200 nm in its largest dimension, and the distance across any pair of particles is substantially less than the wavelength of the light beam. The light directed onto the lens is preferably a beam of circularly polarized light whose plane of polarization is normal to the central axis.

For use in sequencing a linear strand of nucleic acid, the sample may be attached to the substrate surface by stretching the strand linearly, and anchoring opposite end portions of the strands to the substrate. The method further includes translating the lens assembly with respect to the sample on the substrate, to position the nanolens adjacent successive chemical-group bases in the strand. For use in sequencing a plurality of linear strands of nucleic acid samples, the plural strands are stretched and anchored on the substrate in a parallel array. A plurality of such lens assemblies, e.g., an array of cantilever beams is then translated with respect to the array of DNA strands, to position the associated nanolenses adjacent successive chemical-group bases in each of the strands.

These and other objects and features of the invention will be more fully understood when the following detailed description of the invention is read in conjunction with the accompanying drawings.

BRIEF DESCRIPTION OF THE DRAWINGS

FIG. 6a shows frequency dependence of field amplitude in the center of nanolens, corresponding to plasmon resonance at 2.45 eV; FIG. 6b shows field distribution along y axis; and FIG. 6c shows a topographic view of the field distribution as seen from the top;

DETAILED DESCRIPTION OF THE INVENTION

I. Definitions

The terms below have the following meaning, unless otherwise indicated "Plasmon resonant metal" includes any metal, such as gold, silver, or aluminum which can support surface electromagnetic modes—surface plasmon polaritons (SPP), which are coupled modes of photons and plasmons.

"Chemical group" in a sample may include subunits in a polymer, or subunit moieties, such as nucleic acid bases, or chemical substituent groups, such as hydroxyl, amine, alkyl, acid, or aldehyde groups. Such chemical groups are characterized by a unique enhanced Raman spectral signatures or features.

"Gap modes" refers to electromagnetic normal modes or electromagnetic eigenmodes that are excited by external electromagnetic field in a space between two or more plasmon resonance particles and when plasmon resonance particles are placed near (less than 40 nm) from a metal surface, preferably a plasmon resonant metal surface. Examples of plasmon resonance particles are silver or gold particles having their largest dimension typically in the 5 nm to 200 nm size range.

"Gap-mode enhanced Raman spectrum" of a sample refers to spectral features in a Raman spectrum of the sample that are enhanced by the presence of gap modes at the sample.

B. Apparatus for Nano-Spectroscopic Scanning

Figure 1:
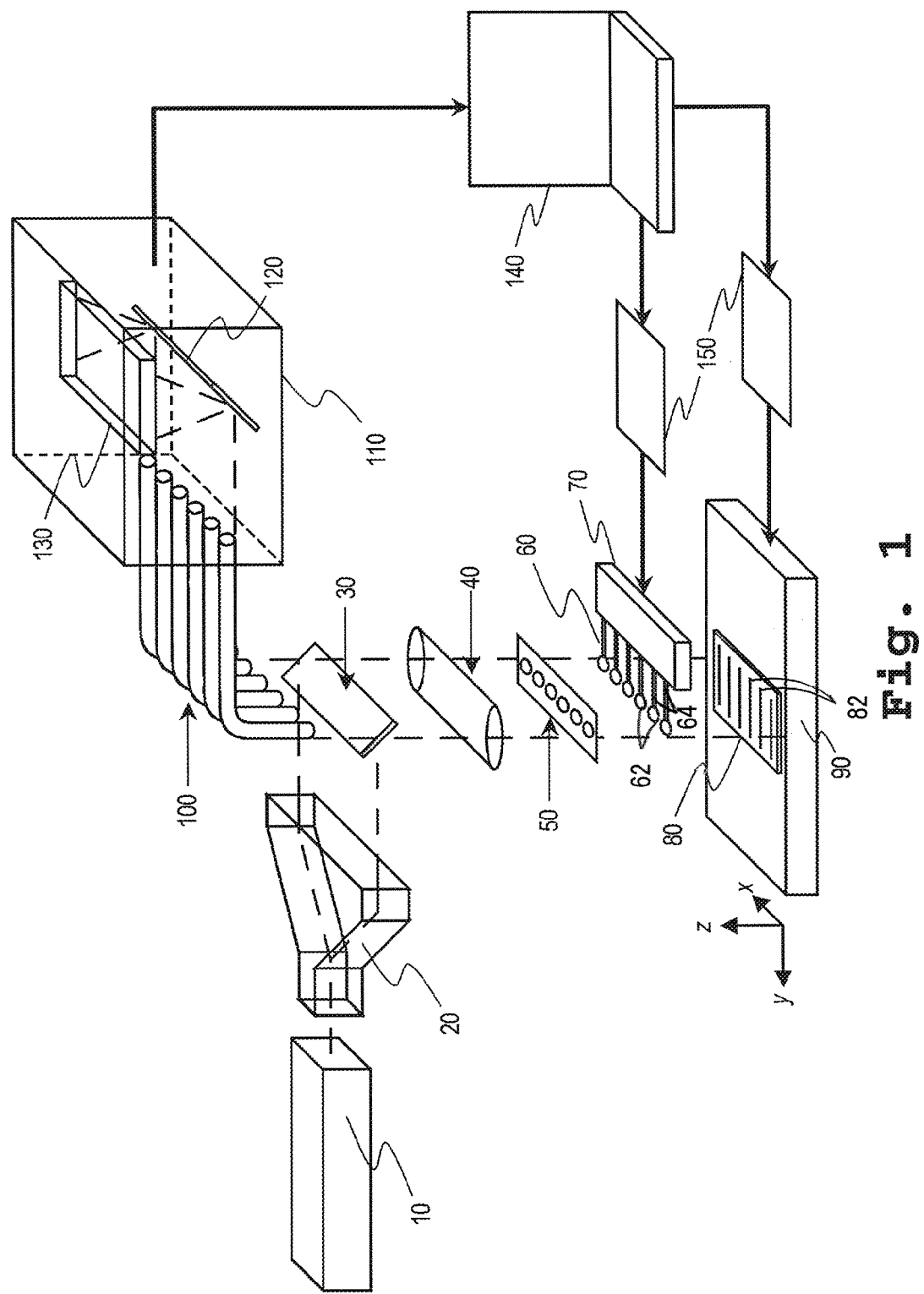
FIG. 1 shows the arrangement of components in an apparatus constructed according to one embodiment of the invention.

FIG. 1 shows an apparatus, indicated generally at 35, for examining the identity of chemical groups in a sample attached to a surface. Shown in the figure is a scanning stage 90, and carried on the stage, a DNA chip 80 having a plurality of stretched DNA strands, such as strands 82 anchored on the chip surface and disposed parallel to one another. Methods for anchoring stretch polymer strands, such as DNA strands on a chip surface will be described below. According to an important feature in this embodiment, the surface of the chip on which the sample is supported has a mirror coating of a plasmon resonance metal, e.g., silver, gold, or aluminum.

The DNA strands are scanned by scanning stage 90 such as a piezoelectric, or electromagnetic motion control stage. A stage with electromagnetic motion control allows a scan area up to tens of centimeters and more, thus allowing scanning single molecule DNA chips with total individual chromosomes.

A light beam with preferably coherent, circularly polarization is generated by a laser 10. The laser may include two lasers for performing nonlinear Raman spectroscopy such as CARS and Femtosecond Induced Raman Spectroscopy (D. McCamant). An exemplary laser system uses a Ti-Sapphire tunable laser with pulsed and continuous mode of operation. The wavelength of excitation light beam preferably is selected and tuned to be in close proximity to the maximum spectral peak in the plasmon resonance absorption spectra of the plasmon resonant substrate. In case scanning with of plasmon nanolens plasmon resonance absorption spectra of whole system (plasmon nanolens+plasmon resonant substrate) should be considered in adjustment of frequency. It is important to note that because of nanoscopic proximity of plasmon nanolens to surface of plasmon resonant substrate spectra of plasmon absorption are changed.

The light beam is expanded by means of beam expander, or is transformed into scanning beam in a beam raster 20. In this way, a single light beam is split into an array of light beams each directed into individual plasmon nanolens in array of nanolens 60. Each individual light beam is directed through a beam splitter 30 and collimation optics 40 onto a microlens array 50. The microlens array allows individual digital control of each individual light beam directed into individual plasmon nanolenses, such as lenses 62 in array 60, carried at the free end of cantilever beams, such as beam 64, as will be described in greater detail below.

As will be appreciated below, the plasmon gap mode nanolens disclosed in the present invention is based on the ability of localized plasmons (collective oscillations of electrons) excited inside metal nanoparticles by external electromagnetic wave to enhance electromagnetic fields in a near-field zone in close proximity to a plasmon resonance surface and to localize it in extremely small nanoscale volumes. This non-propagating electromagnetic field is concentrated in close proximity (few tens of nanometers 30–40 nm) near nanoparticle surfaces and is named as "near field electromagnetic field" to distinguish it from propagating electromagnetic field in far field zones.

With continued reference to FIG. 1, the light beam applied to each plasmon nanolens in the cantilever-beam array may be modulated by a micromachined mirror assembly 50 such as sold by Texas Instruments, Inc., Dallas, Tex., under the tradename "Digital Micromirror Device". This system allows digital control of each individual plasmon nanolens illumination and read out signal scattered from each plasmon nanolens. This system is especially useful for implementing of digital control of high speed programmed individually addressable multichannel pulsed mode illumination and acquisition of scattered signal that is crucial for implementing ultra rapid direct DNA sequencing with direct digitizing of sequence information into computer memory.

A feedback cantilever bending system maintains the distance between the plasmon nanolens and sample DNA. Such controls systems are well known and described for atomic force microscopes, e.g., in U.S. Pat. No. 5,883,705, or near field scanning optical microscopes, e.g., in U.S. Pat. No. 5,354,985, which patents are incorporated herein by reference. One method for of individual actuation and control of each cantilever beam in array 60 during a scanning process employs piezo-resistor feedback control, as disclosed in detail in the U.S. Pat. No. 6,441,359, which is also incorporated herein by reference.

Figure 6A:
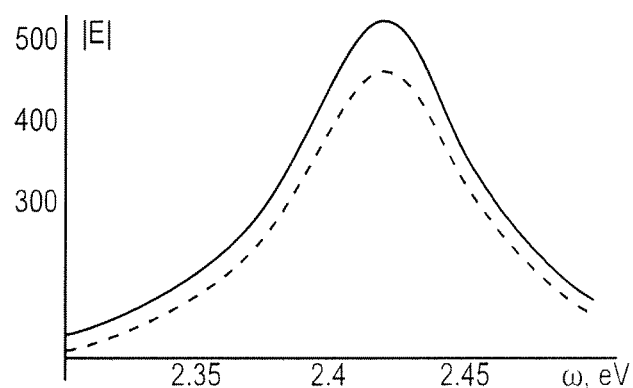
FIGS. 6a, 6b, and 6c show results of numerical simulation of three edge star silver nanolenses.
Figure 6B:
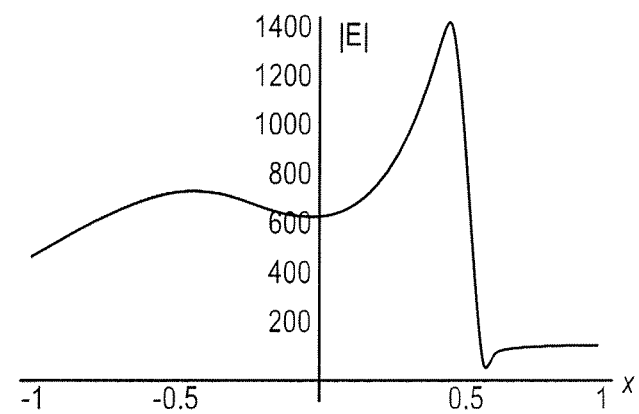

The distance between each plasmon nanolens and the associated DNA sample is preferably maintained at the level of 0.1 nm to few nanometers in order to achieve optimum field amplification and localization in gap between nanolens and DNA sample and surface of substrate by excitation of near field electromagnetic gap modes as it shown on FIGS. 2 and 6a and 6b. As the gap between each nanolens and the substrate surface on which the sample is carried varies, the localization and intensity of electromagnetic gap modes varies also. Therefore, by changing the distance between nanolens and DNA sample (or substrate surface) it is possible to control the shape and localization of electromagnetic gap modes, for the purpose of achieving maximum scattered light (read out) signal and maximum spatial resolution. By optimizing these gap modes, it is possible to achieve a level of resolution that allows discrimination between individual bases in a DNA strand immobilized on the surface of the substrate. Depending on the level of overstretching of the DNA strands on a chip, the requirements for spatial resolution may vary from base to base, and from strand to strand. However, the distance is in a range of a few nanometers to less than 1 nanometer.

In the embodiment shown in FIG. 1, light reflected in backscattering geometry from each plasmon nanolens interacting with individual DNA bases is directed back through microlens array 50, collimation optics 40, and a beam splitter 30 into receiving end of optical fiber ribbon 100. It will be understood, however, that the invention is not limited to backscattering collection of light. In other implementations of invention illumination and collection geometry may be other from backscattering geometry, in which case light illumination and collection optical systems may be separated.

Scattered signal light through optical fiber ribbon 100 is directed onto the slit of a monochromator of a multichannel spectral analyzer 110. Notch filters are employed to eliminate incident light. A diffraction grating 120 splits scattered light beam into set of monochromatic light beams that will be transformed into individual Raman spectra. Spectra obtained on detector array 130 are then converted into digital form and transmitted into computer 140 where they are processed to produce sequence information of DNA samples on the chip. Another suitable optical design, not shown here, utilizes interferometric detection method, such as has been previously disclosed (e.g., F. Zenhausen).

C. Nanolens Operation and Fabrication

This section describes specific nanolens structures designed to be placed in close proximity to the smooth metallic surface of the sample substrate, to produce localized gap modes when the lens is illuminated by a a light beam, e.g., a coherent and/or circularly polarized light beam. These modes can be used for direct optical reading of molecules, placed in a space between the nanolens of mirror substrate surface, with high spatial resolution for achieving sub-nanometer resolution, and with signal amplification allowing detection of spectral signature of single small molecule such as individual bases of DNA strands.

The most general design of a nanolens includes one and preferably a plurality (e.g., 2–6) metal nanoparticles having selected shapes and selected particle geometries with respect to each other. A preferred particles geometry is a symmetrical arrangement of the particles about a central axis, as will be illustrated below, although other geometries, such as disordered fractal, are also contemplated. The nanoparticles forming the lens may have different shapes and dimensions and are placed in nanoscopic proximity to each other. However the largest dimension of each nanoparticle and of the system as a whole do not exceed the wavelength of the illuminating light. Nanoparticles in the size range between 5–200 nm, e.g., 20–50 nm are preferred.

FIG. 2 is a detailed perspective view of a portion of a cantilever beam 160 carrying a six-particle nanolens 180 at its free (distal) end. As seen, a circularly polarized light beam 190 from laser source is directed through confocal lens optics 50 onto a nanolens 180. The nanolens is mounted on a holder 170 formed of transparent dielectric material, which could be in one embodiment the free end of cantilever 160 used to controls the distance between a nanolens and the sample in scanning probe device. The nanolens is placed in close proximity to a metal mirror surface 200 on the sample substrate. Since far field light directed by the confocal optics can be focused to a spot size around or slightly less than 1 micron, which is determined by diffraction optics limit, and diameter of the nanolens (the diameter of the circle circumscribing the nanolens particles 182) is preferably in the range of 50–200 nm, that is, less than the wavelength of the illumination light. Also as seen in the figure, the light illumination area (dotted-line circle indicated at 350) is usually larger than area of nanolens. However, it is possible to create a nanolens of 0.5–1.0-micron diameter so that it will match focal spot. In that case, the nanolens will work as a nanoantenna, which will concentrate electromagnetic energy to the center of nanolens through excitation of localized plasmons.

Figure 2A:
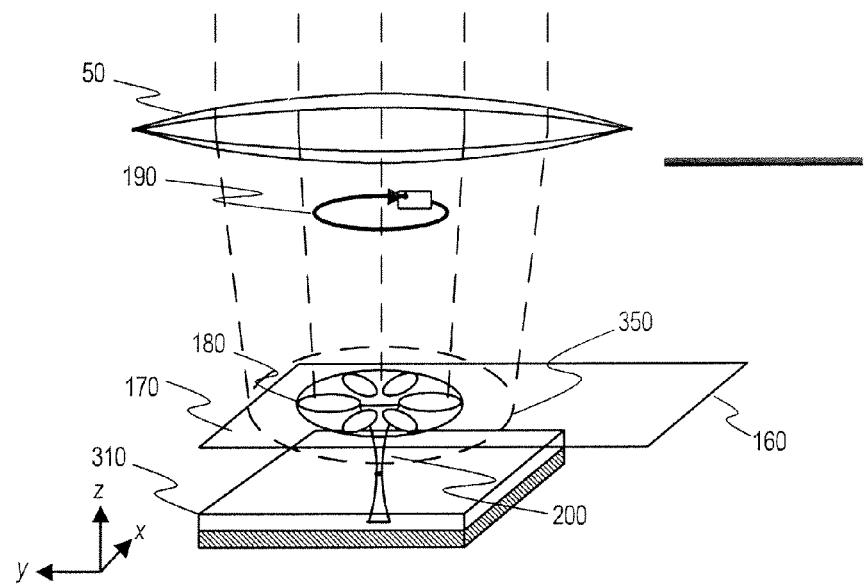
FIG. 2a illustrates electromagnetic phenomena resulting in near-field electromagnetic gap modes by directing a circularly polarized light beam onto a nanolens constructed according to one embodiment of the invention having a six-particle nanolens.
Figure 2B:
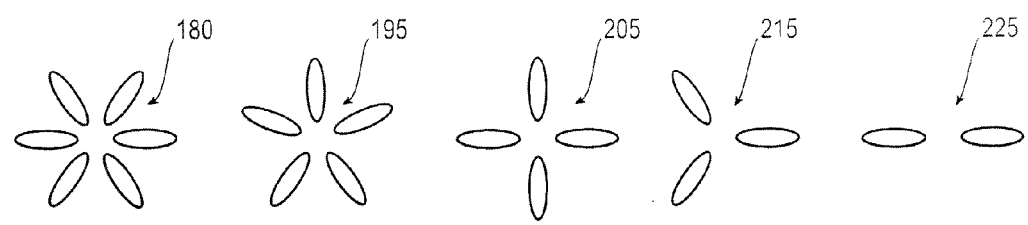
FIG. 2b shows nanolenses formed of between 2 and 6 PRPs.

In the embodiment shown in FIG. 2a, plasmon nanolens 185 has a star like structure consisting of six metal nanoparticles, such as particles 182, each particle having a shape of either a prolate spheroid with a large eccentricity (preferably more than 5), or a cylindrical nanorod with hemisphere caps at the ends, or a metal nano wire. This particle geometry is also seen at 185 in FIG. 2B, along with nanolens particle configurations 195, 205, 215, and 225 for lens with five, four, three, and two particles, respectively.

As noted above, illumination of each nanolens is preferably by a laser beam or non-coherent electromagnetic wave with circular polarization. Maximum enhancement of the electromagnetic field, indicated at 200 in FIG. 2a, is achieved in the central part of the lens close to axis of nanolens. This region has diameter of a few nm or less. Field amplification factor up to 1500–3000 may be achieved in the center of nanolens as it is illustrated by results of numerical simulation described below with respect to FIGS. 6a–6c, 7a–7c, and 8 8, below. That amplification factor significantly exceeds the amplification achievable in configurations consisting of spherical nanoparticles and other shapes of nanoparticles known from prior art. Maximum local field amplification achieved in numerical simulation of 300 was reported (H. Xu).

The nanolens of the invention may be constructed by a variety of known methods. In general, the nanolens is fabricated integrally with the cantilever beam using established nanofabrication methods based on electron beam lithography or focused ion beam lithography (G. R. Brewer), or based on Scanning Tunneling Microscopy Lithography. Another method of fabrication may be based on template assisted self-assembling (Y. Xia). Alternative methods such as dip-pen nanolithography can be used to create plasmon nanolens patterns on different support materials (e.g., D. Ginger) or DNA based self-assembling technique (e.g., C. M. Niemeyer). In one embodiment plasmon nanolens may be integrated into at free end of cantilever that is part of scanning probe device, and can simultaneously perform function of cantilever tip that control distance between nanolens and sample during scanning in scanning probe devices such as Atomic Force Microscope—AFM or Scanning Near Field Optical Microscope—SNOM. One possible implementation of plasmon nanolens integrated into cantilever of scanning probe spectroscopic device is presented in FIG. 3.

Figure 3A:
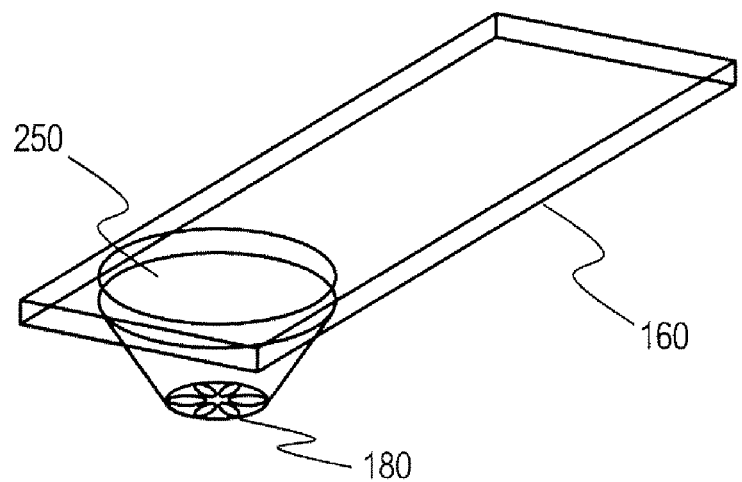
FIGS. 3a and 3b shows in perspective (3a) and cross-sectional (3b) views, an end region of a cantilever beam having an integrated nanolens, in accordance with the invention.
Figure 3B:
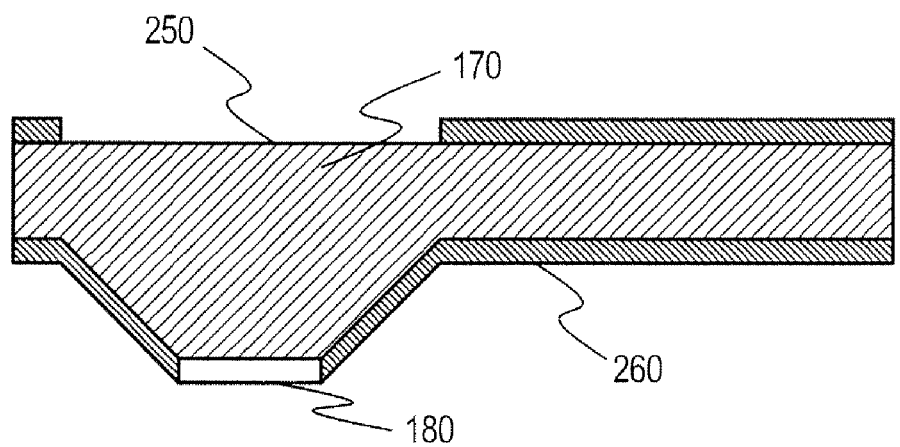

FIG. 3 illustrates how plasmon nanolens may be integrated into a free end of cantilever of scanning probe spectroscopic device, and can simultaneously perform the function of a cantilever tip that control distance between the nanolens and sample during scanning of the sample. Cantilever 160 is prepared from a composite material that has an opaque material portion 260 and an optically transparent portion 170 that forms optical window 250, allowing incident circularly polarized light to interact with nanolens 180 and to excite effectively localized plasmas (LP) and gap modes (GM).

D. Preparation of Sample-Containing Substrate

The substrate or support in the apparatus is designed to enhance electromagnetic field in close proximity to surface, and is coated with a thin film of a plasmon resonant material, such as a silver, gold, or aluminum. Film thickness is preferably between 25–200 nm, e.g., 50 nm. Suitable substrate, e.g., glass substrates can be coated with the metal film by known methods, such as vacuum evaporation or rf sputtering techniques. Exemplary substrate coatings and methods of their production are disclosed in U.S. Pat. No. 5,611,998 for "Optochemical sensor and method for production," which patent is incorporated herein by reference and in the reference to V. Matyushin, also incorporated herein by reference.

DNA strands with lengths, for example, from 100 nanometers up to 2.5 millimeters are placed on a substrate as shown at 82 in FIG. 1. The distance between strands should be in the range of 200–300 microns and should correspond to the distance between adjacent cantilevers in cantilevers array. Preferable is distance 250 micron, which correspond to pitch of 250 micron, which is standard pitch in optical-fiber ribbon applications.

Figure 4:
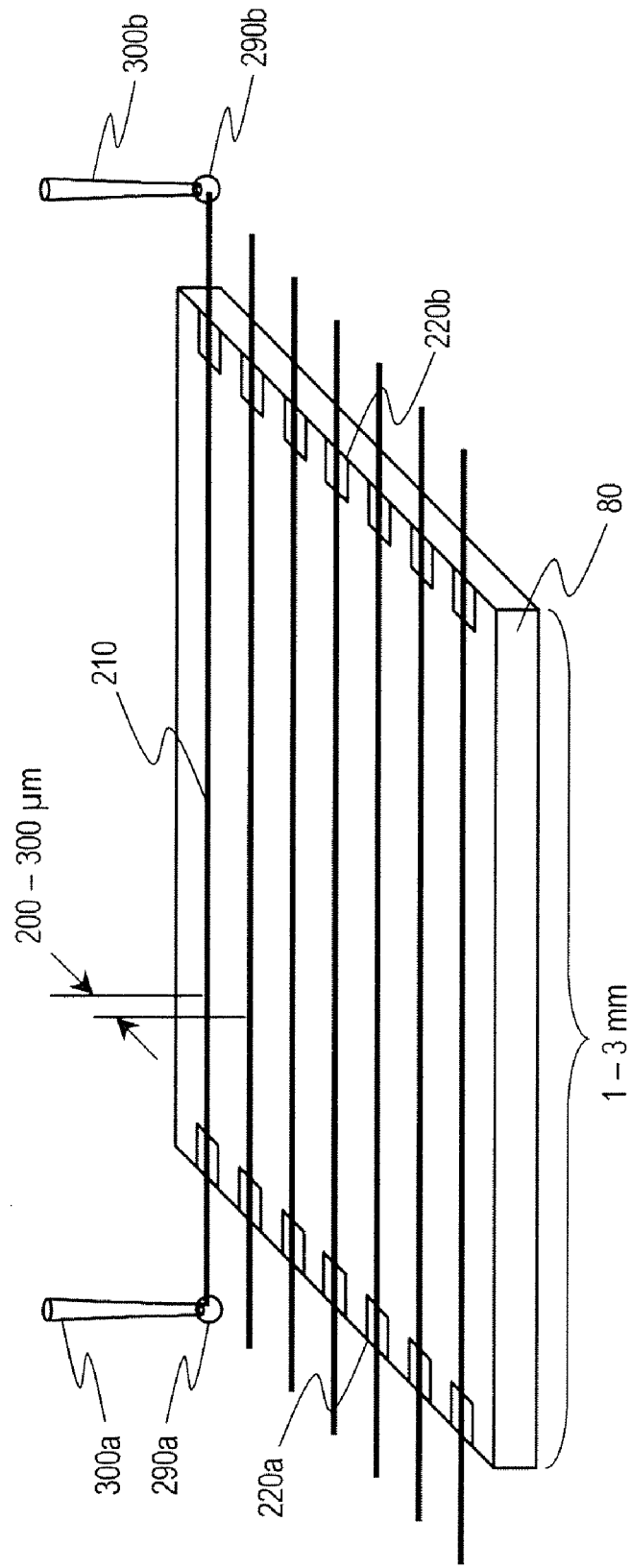
FIG. 4 shows a substrate having an array of stretched DNA strands anchored on its upper surface.

FIG. 4 shows an exemplary chip or substrate 80 for use in the apparatus and method of the invention. As shown here, samples of DNA obtained, for example, from genomic DNA, in the form of single-stranded DNA fragments with lengths up to 2.5 millimeters (5 Mbase). The strands, such as indicated at 210 are placed onto surface of slide with plasmon resonant optical enhancement properties 80. They are placed in an ordered, addressable way. Each end of DNA strand is attached to complimentary oligonucleotide on right/left barcode 220a and 220b. The distance between strands should be in the range of 200–300 microns and should correspond to the distance between adjacent cantilevers in cantilevers array. Preferable is distance 250 micron, which correspond to a pitch of 250 micron, which is in correspondence with pitch in standard optical-fiber ribbon.

Methods for stretching and orienting linear polymer samples, such as DNA, RNA, nucleic analogs, polypeptides, linear carbohydrates and the like, are known. For example, the opposite ends of the sample polymer, e.g., DNA, can be covalently attached to microspheres, such as latex or glass beads, and the beads are then manipulated by pulsed-laser molecular tweezers until a suitable degree of stretching, and preferably overstretching, is achieved. This approach is illustrated in FIG. 4 which shows microspheres 290a, 290b attached to opposite ends of DNA strand 210. Each sphere is "captured" by a laser beam, such as beams 300a, 300b, for manipulating the spheres to stretch and orient the strand for placement on the substrate surface. Once this placement is achieved, end regions of the strand are anchored to the substrate by hybridization with complementary oligonucleotides attached to the bar-code region of the substrate. Methods for capturing and manipulating microspheres in a laser beam are described, for example, in U.S. Pat. No. 5,620,857 and in U.S. patent application 20040001371, both of which are incorporated herein by reference.

In a related approach, the ends of the polymer strand are covalently attached to magnetic beads, or to a solid support and a magnetic bead, and magnetic field(s) are applied to the bead(s) until an appropriate degree of stretching and strand orientation are achieved. More generally, the opposite ends of a strand may be attached to a pair of relatively moving supports, and the supports positioned until a desired degree of stretching and orientation are produced, as disclosed, for example, in U.S. Pat. No. 6,342,353, which is incorporated herein by reference.

Methods for drawing a charged polymer strand into a linear conformation by electrophoresis in a narrow microchannel are also known.

Once the polymer strands are stretch and oriented for attachment to the substrate, the sample molecule is anchored on the substrate by any of a number of suitable anchoring methods. As noted above, the substrate may be provided by end-regions oligonucleotides capable of hybridizing to the sequences at end regions of a sample DNA strand. Where the strand is stretched by manipulating particles covalently attached to the strand ends, the substrate may contain chemical groups or magnetic structure for anchoring the particles to the substrate, with the strand in a stretched condition. One common chemical attachment chemistry for a gold surface is a thiol reagent covalently carried at end regions of the sample strand.

More generally, procedures for preparation of a substrate surface on which DNA molecules are to be anchored are known to those of skill in the art of DNA hybridization detection methods (See for instance, J. P. Rabe).

E. Scanning and Detection Method

As indicated above, an important application of the apparatus and method of the invention is in sequencing nucleic-acid samples such as chromosomal or full genomic DNA. This section will describe the operation of the above apparatus and the method of the invention with reference to this particular application, it being understood that the same operation and method will apply to the examination of the chemical groups in any sample.

At its simplest, the method is used to examine one or more chemical groups of a single molecule or collection of similar molecules localized at a defined detection region on a substrate. In this application, a single nanolens carried, for example, at the free end of a cantilever beam is moved toward the sample, e.g., in the distance range less than 10–40 microns, until a maximum enhancement of a distinguishing enhanced Raman spectral feature is observed. Alternatively, the spectral features may be recorded as the nanolens is moved alternately toward and away from the sample surface, to yield a time-variant spectrum of the sample. Nanolens oscillation in the range of between 0.1 to 10 nm, for example, could be used in generating the time-variant spectrum.

More generally, the method of the invention for examining the identity of chemical groups in a sample, includes the steps of first attaching the sample to a substrate having a mirror surface on which the sample is supported, and which is formed of a plasmon resonant metal. A beam of light is directed onto a nanolens of the type described above to produce near-field electromagnetic gap modes in a space between the nanolens and a confronting detection region on the substrate surface, when the gap between the nanolens and substrate is 30 nm or less. The lens assembly is then moved toward or away from the substrate surface, with a spacing between the nanolens and substrate surface of less than 40 nm, to produce electromagnetic gap modes that enhance the Raman spectroscopy signals produced by the sample in the detection region. Light emitted by or scattered from the sample at the detection region is received by a detected and converted into a gap-mode enhanced Raman spectrum, whereby the sample chemical group at the detection region can be identified.

Where the sample contains a plurality of groups arranged along a linear portion of the sample molecules, as in the case of a nucleic sample for identification of successive base groups, the procedure just described is applied to each base successively, as the nanolens is moved relative to the substrate. This movement may be carried out by cantilever translation relative to a stationary substrate of substrate stage movement relative to a stationary nanolens. As the nanolens is placed at each successive position, it is then moved toward or away from the sample to find the optimal detection distance, or to generate a time-variant spectrum, as described above. The lens and sample bases may be kept in registry by one of a variety of registration techniques. For example, a "control" nanolens could track the detect bases in a known-sequence DNA sample carried on the substrate. By tracking this sequence, along with one or more unknown-sequence samples, the apparatus can confirm that the relative movement between lenses and substrate is acting to preserve registration between sample and successive DNA bases. Alternatively, one of the cantilever beams in the apparatus may be a scanning atomic-force microscope tip for detecting movement of the tip over each base of a control DNA strand, as the array of cantilever devices are moved along the DNA strands.

Figure 5A:
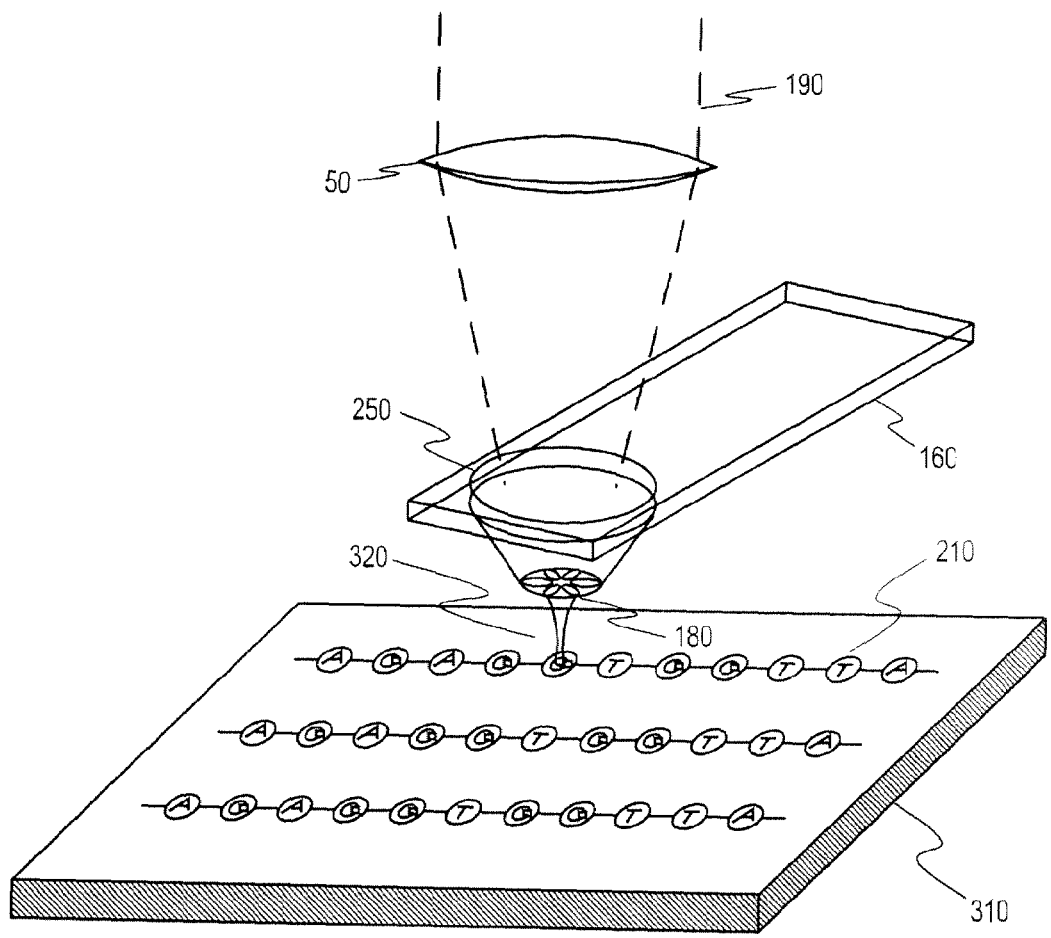
FIGS. 5a and 5b illustrate in perspective (5a) and sectional view (5b), the optical phenomena exploited in the present invention for detecting successive individual bases in a stretched DNA sample.
Figure 5B:
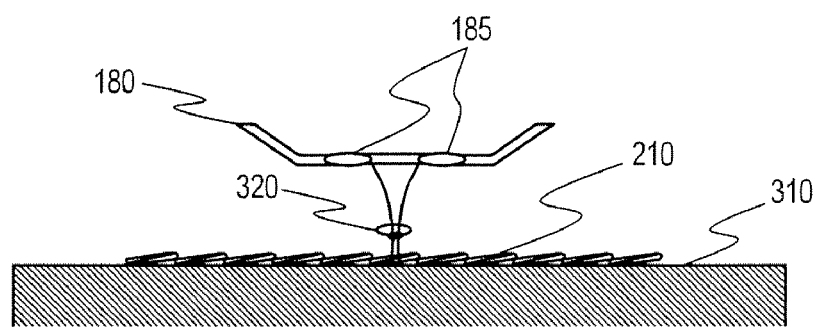

In a more usual application, a plurality of linear sample strands, e.g., DNA strands are aligned on a single substrate, for simultaneous reading by a plurality of nanolenses, as illustrated at 82 in the apparatus of FIG. 1. FIGS. 5a and 5b illustrate this operation as applied to reading a plurality of stretched, aligned DNA strands, such as strand 210, carried on a substrate 310. Although the figures show a single lens assembly composed of a cantilever beam 160 carrying a nanolens 180 at its free end, it will be understood that the apparatus includes an array of lens assembly, one for each of the aligned strands on the substrate.

As the group of lens assemblies are moved along the substrate, each lens assembly is adjusted vertically (in a direction toward the substrate) to optimize spectral signal. As seen in FIG. 5b, this vertical movement is effective to place the gap modes produced by the concentration of near-field electromagnetic modes between the lens, formed by PRPs such as at 185, with the plasmon resonant surface, indicated at 310.

The enhanced Raman spectra of each strand chemical group (base) are consecutively measured using a multichannel Raman spectrograph and are digitized by means of two-dimensional ICCD array with digital recording. The signal from the Raman spectrometer is stored in computer memory for further analysis. The final results are obtained in a form of sequence of bases of nucleotides A,T,G,C. In a course of scanning procedure nanolens—tip will detect each base (A,T,G,C) in DNA strands both spectroscopic and topographically.

SERS spectra are registered consecutively for each base which will allow identifying each particular base (A,T,G,C) in DNA strand by its unique enhance spectral signature that is characteristic of that base, allowing direct de novo sequencing of individual fragments of DNA molecule. SERS spectra of A, T, G, and C obtained on plasmon resonant substrate are known to give distinctive spectra that allow for the different bases to be identified. The present invention, by focusing the excitation field in a small gap between a lens and substrate, and exploiting gap-mode enhancement of the Raman signals, allows individual bases of DNA to be identified, thus permitting direct base-by-base DNA reading.

The numbers of cantilevers with fiber optic tips which can be used in array, are in principle unlimited; however, for one scan sequencing of the largest human chromosome (Human Chromosome No 1 containing about 263 million bases), the apparatus would require about 100 lens assemblies, each reading a fragment of about 2.5–3.0 Mbase. Assuming 0.01 sec sampling time, the apparatus would complete sequence of this chromosome in less than about 10 hour of scan time. Using this device practically it is possible to implement in parallel up to few hundred channels in array (1 DNA strands per channel) with sampling speed of 0.01 to 1 second per base.

More generally, the method of the invention for examining the identity of chemical groups in a sample, includes the steps of first attaching the sample to a substrate having a mirror surface on which the sample is supported, and which is formed of a plasmon resonant metal. A beam of light is directed onto a nanolens of the type described above to produce near-field electromagnetic gap modes in a space between the nanolens and a confronting detection region on the substrate surface, when the gap between the nanolens and substrate is 4 nm or less. The lens assembly is then moved toward or away from the substrate surface, with a spacing between the nanolens and substrate surface of less than 40 nm, to produce electromagnetic gap modes that enhance the Raman spectroscopy signals produced by the sample in the detection region. Light emitted by or scattered from the sample at the detection region is received by a detected and converted into a gap-mode enhanced Raman spectrum, whereby the sample chemical group at the detection region can be identified.

Figure 6C:
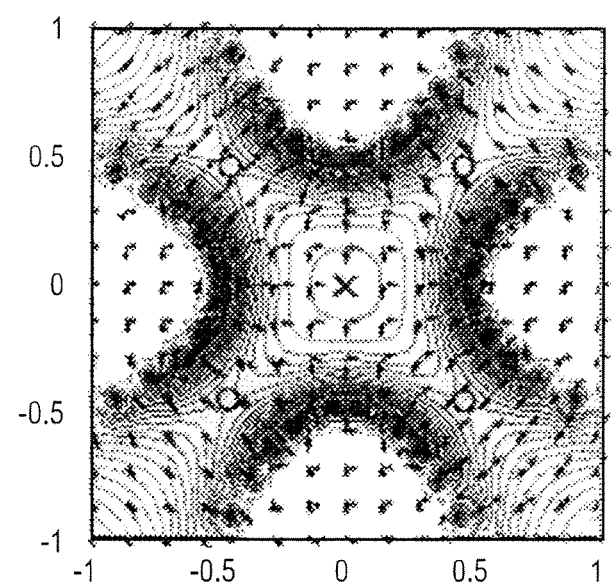
Figure 7A:
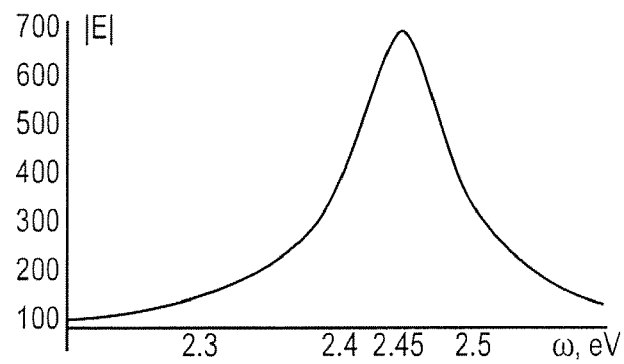
FIGS. 7a, 7b, and 7c are like FIGS. 6a–6c, respectively, but show results of numerical simulation of a four edge star silver nanolens.
Figure 7B:
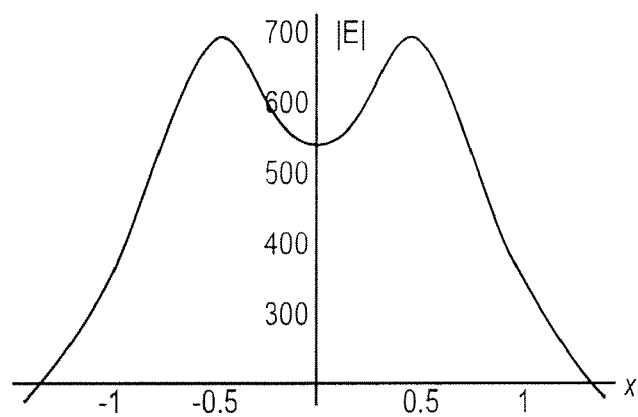
Figure 7C:
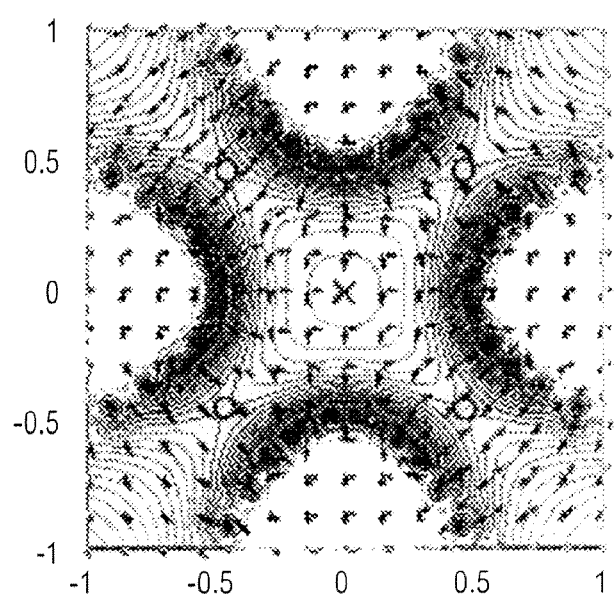
Figure 8:
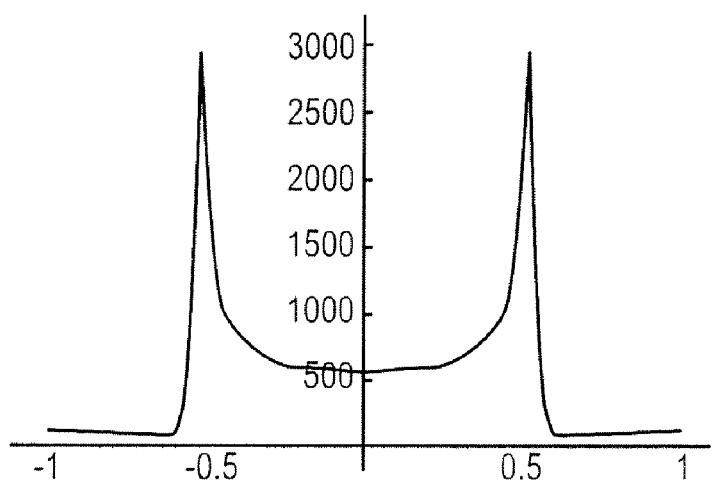
FIG. 8 shows distribution of field in a four edge star nanolens along x axis, showing a maximum amplification of 3000 near the surface of PRP.

The degree of Raman spectra amplification achievable with the present invention can be appreciated from FIGS. 6–8. In these figures, electromagnetic field strength E was calculated by modeling the system and solving Maxwell's equations in a near-field approximation using an integral equation approximation. FIG. 6a shows the variation in E as a function of eV for a three-particle lens. The field distribution in the central region of the lens is shown in FIG. 6C. FIG. 6b is a plot of field strength taken along the y axis in FIG. 6C, along the line x=0. As seen, field strength amplification reaches a maximum of about 1,400 (amplification over incident light) at the point y=0.5, close to the upper particle in FIG. 6c.

A similar set of plots is shown in FIGS. 7a–7c, but where the lens here is constructed of four symmetrical particles, as seen from the field distribution diagram in FIG. 7c. FIG. 7b shows a symmetrical distribution of E along the line x equal zero as the y coordinate varies from the bottom to the top. When the plot is constructed along the diagonal line between −1, −1 and +1, +1, the plot seen in FIG. 8 is achieved, showing an amplification of nearly 3000 at points near between the particles away from the center.

According to prevailing mechanism, Raman enhancement is electromagnetic mechanism, where Raman signal is proportional to $E^4$ (M. Moskovits, Rev. Mod. Phys. v. 57, p. 783, 1985) where E is local enhancement of field in the area of molecule. In the case of a field amplification factor 500, the Raman signal enhancement would be $500^4 = 6.25 \; 10^{10}$, which is significantly higher than has been reported in the literature. To obtain this enhancement, the sample molecule should be in center of a multi-particle nanolens. However, if the molecule is also close to a plasmon resonance surface, the field enhancement can be as high as 3,000, giving a Raman signal enhancement of up to $8.1 \times 10^{13}$, allowing single molecule chemical groups to be detected.

Although the invention has been described with respect to particular embodiments and applications, it will be understood that various changes and modification may be made without departing from the invention.

F. Plasmon Nanolens in Combination with a Nanopore Device

Figure 9:
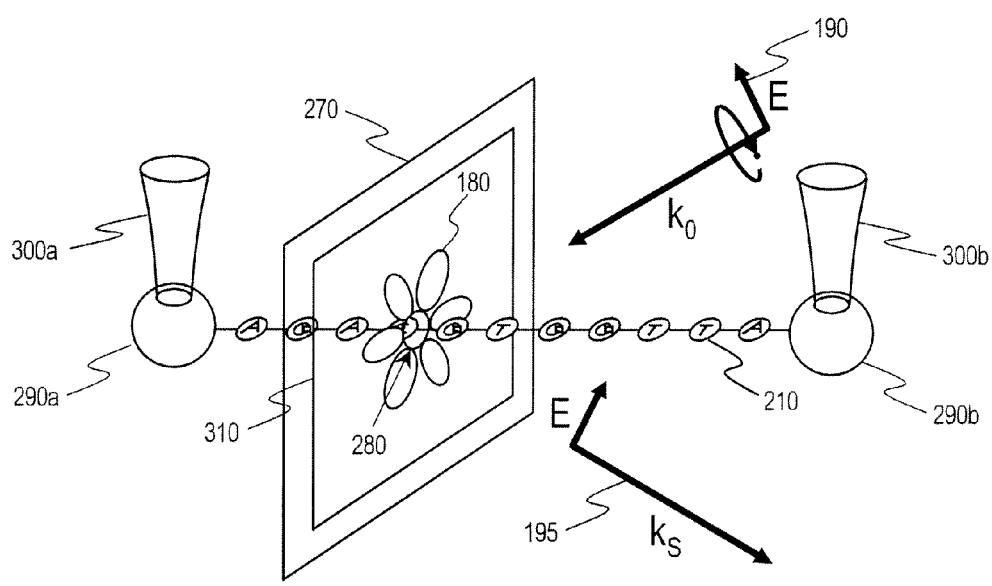
FIG. 9 illustrates a plasmon nanolens in combination with nanopore device.

Another way to read spectroscopically a sequence of long length biopolymer macromolecules (like DNA, RNA, or a polypeptide) by using the Raman plasmon nanolens of the invention is to pull a biopolymer molecule through a nanometer-size hole at which the nanolens is mounted, as illustrated in FIG. 9.

With reference to this figure, a biopolymer (DNA strand) 210 is pulled through an artificial nanopore 280 by means of electric field (electrophoretic or electroosmotic method). Examples of artificial nanopore devices are disclosed, for example, J. Li et al. "DNA molecules and configurations in a solid-state nanopore microscope", Nature Materials, Vol. 2, p. 611–615 (2003), and in D. Hansford, and Mauro Ferrari, U.S. Patent Application Publication US20030205552A1, Nov. 6, 2003. In these devices, the speed of bases passing through the nanopore may be very high—in a range of million bases per second—but may be modulated according to the electric field applied and the electrolyte composition of the medium, as disclosed in the above references.

In another embodiment, mechanical manipulation by a DNA biopolymer with laser or magnetic tweezers 300a and 300b may be used. The speed of monomer translocation through nanopore 280 can be controlled within a broad range, and may be reduced to thousands or monomer per second, which is suitable for Raman spectroscopic detection of monomers using a plasmon nanolens. Illuminating beam from laser source 190 is used to excite enhanced Raman signal from the DNA bases (monomers). The mechanism of enhancement is as described above and is due to field localization and enhancement by excitation of Gap Modes—GM in two ways: between different plasmon nanoparticles constituting nanolens 180, and between plasmon nanoparticles 180 and plasmon resonant substrate 310 which is placed on the membrane from a dielectric material 270. Scattered signal 195 is collected by optical lens and analyzed by Raman spectrometer, as above.

An important advantage of this method over that described in above is that it eliminates Brownian motion and still retains the biopolymer in solution, thus avoiding difficulties related with biopolymer (DNA) manipulation on solid surfaces. Reducing or elimination of Brownian motion is a useful for efficient operation of the plasmon nanolens used for Raman spectroscopic detection of each individual monomer by discrimination of chemical groups unique for each monomer.

Figure 10:
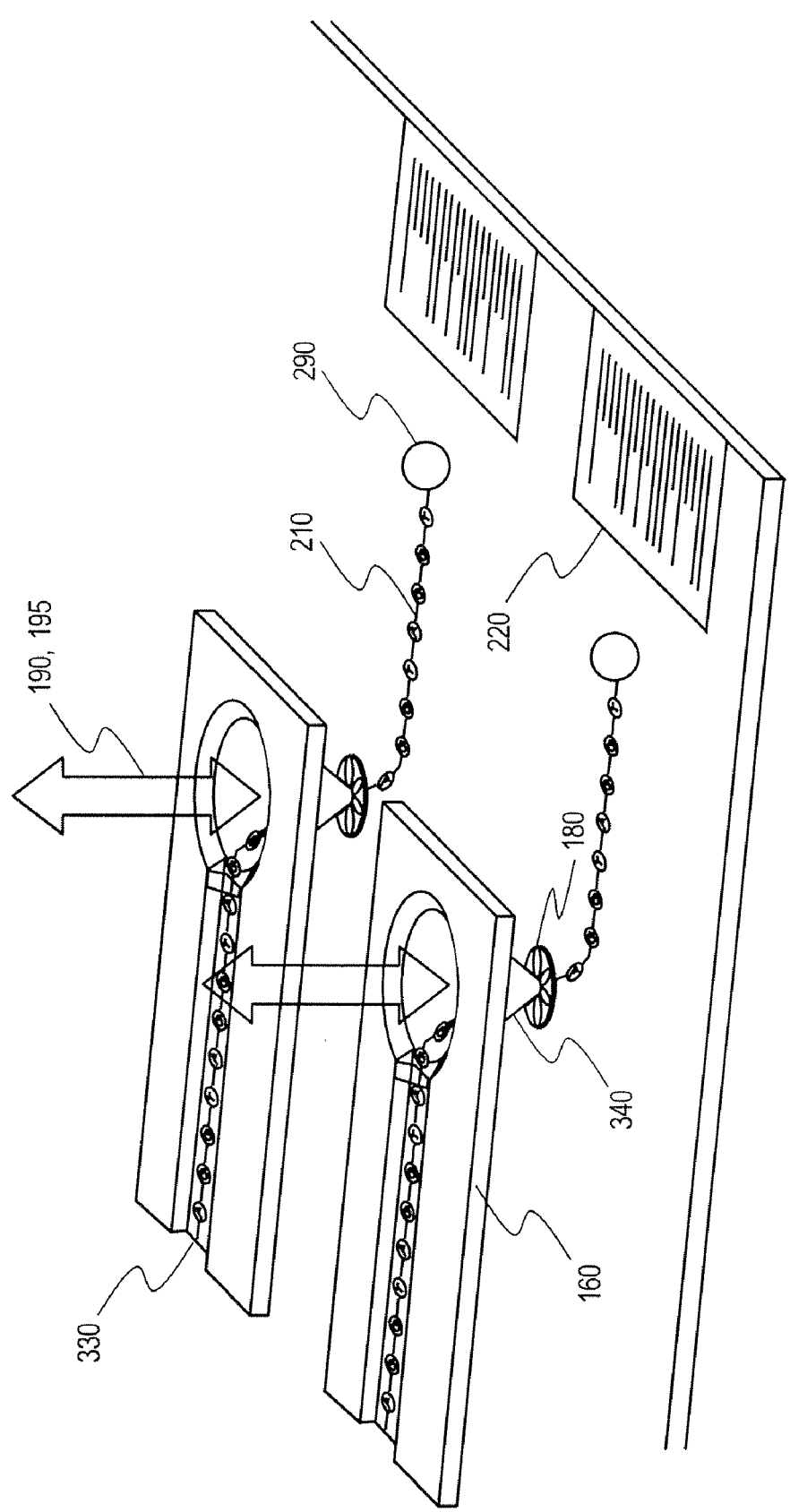
FIG. 10 illustrates a plasmon nanolens in combination with a scanning device having an array of tips

G. Use of Plasmon Nanolens in Combination with a Scanning Device with an Array of Fountain Tips Another embodiment of the invention is illustrated at FIG. 10. DNA strand 210 can be attached to surface of sold substrate by using polymer anchor 290. Attachment may be done in addressable way using a complementary oligonucleotides barcode 220 patterned on slide surface. A nanopore with a nanolens 180 is mounted at the free end of cantilever fountain tip 340 with a hole in it (nanopipette design) that is placed on the cantilever 160 of a scanning device. In this case speed of biopolymer movement is also controlled by scanning speed of scanning device and may be changed within a wide range. The cantilever tip should be made as a fountain type having a nano-hole in the apex end. One example of an array scanning device that may be used in the present invention is disclosed in Eric Henderson's et al U.S. Pat. No. 6,716,578, Apr. 6, 2004, and. J. Xu et al. "Microfabricated Quill-Type Surface Patterning Tools for the Creation of Biological Micro/Nano Arrays", Biomedical Microdevices, v. 6, p. 117–123 (2004). Raman spectra are collected by illumination of nanolens 180 from the top of the cantilever using a laser beam 190, and by collecting back scattered beam 195 which is analyzed in a Raman spectrometer. The cantilever has a channel 330 in which DNA strands 210 are located during scanning process.

Precise tuning of a nanolens mounted on a nanopore hole may be achieved by using multiple beam optical tweezer as it is disclosed for example in (J. Prikulis et all, Nano Letters, v. 4, p. 115–118, 2004).

Although the invention has been described with respect to particular embodiments and applications, it will be appreciated that various changes and modifications may be made without departing from the invention as claimed.

The invention claimed is:

1. Apparatus for examining the identity of chemical groups in a sample attached to a surface, comprising
    a substrate having a mirror surface on which the sample is supported, and which is formed of a plasmon resonant metal,
    a source of a beam of light,
    a lens assembly having a tip region and a nanolens composed of one or more plasmon resonance particles disposed on the tip region, and arranged thereon to produce, when the light beam is directed through the nanolens, near-field electromagnetic gap modes in a space between the nanolens and a confronting detection region on the substrate surface, in a gap between the nanolens and substrate that is 40 nm or less,
    a focusing mechanism for moving the lens assembly toward and away from the substrate surface, with a gap of less than 40 nm, to produce electromagnetic gap modes that enhance the Raman spectroscopy signals produced by the sample in the detection region;
    a detector for receiving light emitted by or scattered from the sample at the detection region, and for converting the received light into a gap-mode enhanced Raman spectrum, whereby the sample chemical group at the detection region can be identified, and
    a translation mechanism for translating the lens assembly relative to said substrate, to position the lens assembly over different detection regions of the substrate.

2. The apparatus of claim 1, wherein the nanolens in said assembly includes at least said three plasmon resonance particles arranged symmetrically about a central axis that is normal to the plane of the substrate surface, each particle is less than 200 nm in its largest dimension, and the distance across any pair of particles is substantially less than the wavelength of the light beam.

3. The apparatus of claim 2, wherein said particles are spherical.

4. The apparatus of claim 2, wherein said particles are ellipsoidal and arranged with their major axes oriented to intersect said central axis.

5. The apparatus of claim 2, wherein said light source produces a beam of circularly polarized light whose plane of polarization is normal to said central axis.

6. The apparatus of claim 1, wherein said lens assembly includes a cantilever beam having a tip region at its free end.

7. The apparatus of claim 6, wherein said focusing mechanism includes a piezo-electric driver operatively coupled to said beam.

8. The apparatus of claim 7, wherein said focusing mechanism is operative to bring said nanolens to a selected distance between 0.1 and 5 nm of the substrate surface.

9. The apparatus of claim 1, wherein said translation mechanism includes a piezoelectronic drive.

10. The apparatus of claim 1, for use in sequencing a linear strand of nucleic acid, by examining the chemical-group bases of the nucleic acid strand, wherein the substrate includes molecular anchors for holding the nucleic acid strand in a stretched linear condition, and the translation mechanism is operable to move the lens assembly along the length of the strand, for examining and identifying each base of the strand sequentially.

11. The apparatus of claim 10 for examining a plurality of substantially linear samples simultaneous, which includes a plurality of linearly aligned cantilever lens assemblies, each of whose position toward and away from the substrate surface can be individually controlled by a corresponding focusing mechanism associated with each lens assembly, and which are translated as a unit by a single translation mechanism.

12. The apparatus of claim 11, for use in sequencing a plurality of linear strands of nucleic acid, by examining the chemical-group bases of the nucleic acid strands, wherein the substrate includes molecular anchors for holding each of the nucleic acid strands in a stretched linear condition, and the translation mechanism is operable to move the lens assembly along the lengths of the strands, for examining and identifying each base of the strands sequentially.

13. A method for examining the identity of chemical groups in a sample, comprising
attaching the sample to a substrate having a mirror surface on which the sample is supported, and which is formed of a plasmon resonant metal,
directing a beam of light onto a nanolens in a lens assembly having a tip region and a nanolens disposed on the tip region and composed of one or more plasmon resonance particles which are arranged on the tip region to produce near-field electromagnetic gap modes in a space between the nanolens and a confronting detection region on the substrate surface, when the gap between the nanolens and substrate is 30 nm or less,
moving the lens assembly toward or away from the substrate surface, with a spacing between the nanolens and substrate surface of less than 30 nm, to produce electromagnetic gap modes that enhance the Raman spectroscopy signals produced by the sample in the detection region;
receiving light emitted by or scattered from the sample at the detection region, and
converting the received light into a gap-mode enhanced Raman spectrum, whereby the sample chemical group at the detection region can be identified.

14. The method of claim 13, wherein said moving is carried out to bring said nanolens to a selected gap distance between 0.1 and 5 nm of the substrate surface.

15. The method of claim 13, wherein said directing includes directing the light beam onto a nanolens composed of at least said three plasmon resonance particles arranged symmetrically about a central axis that is normal to the plane of the substrate surface, each particle is less than 200 nm in its largest dimension, and the distance across any pair of particles is substantially less than the wavelength of the light beam.

16. The method of claim 15, wherein said directing includes directing onto said lens, a beam of circularly polarized light whose plane of polarization is normal to said central axis.

17. The method of claim 15, for use in sequencing a linear strand of nucleic acid, wherein said attaching includes stretching the strand linearly, and anchoring opposite end portions of the strands to said substrate, and which further includes translating the lens assembly with respect to the sample on the substrate, to position the nanolens adjacent successive chemical-group bases in the strand.

18. The method of claim 17, for use in sequencing a plurality of linear strands of nucleic acid samples, wherein said attaching includes anchoring the samples in a plurality of parallel strands, and said translating includes translating the lens assembly with respect to the samples on the substrate, to position the nanolens adjacent successive chemical-group bases in each of the strands.

* * * * *